United States Patent [19]

Nógrádi et al.

[11] Patent Number: 4,599,327
[45] Date of Patent: Jul. 8, 1986

[54] DIBENZO[BD]PYRAN DERIVATIVES, PROCESS FOR THE PREPARATION THEREOF AND PHARMACEUTICAL COMPOSITIONS CONTAINING SAME

[75] Inventors: Mihály Nógrádi; Dezsö Korbonits; Ágnes Gottsegen; Sándor Antus; Zsuzsa Fürst; József Knoll; József Szejtli; Ágnes Stadler; Gábor Kovács, all of Budapest; Katalin Mármarosi, Biatorbágy, all of Hungary

[73] Assignee: Chinoin Gyogyszer es Vegyeszeti Termekek Gyara RT, Budapest, Hungary

[21] Appl. No.: 557,629

[22] Filed: Dec. 2, 1983

[30] Foreign Application Priority Data

Dec. 3, 1982 [HU] Hungary .................... 2251/3884

[51] Int. Cl.[4] .............. A61K 31/70; C08B 37/16
[52] U.S. Cl. .................... 514/58; 536/103; 536/46; 549/280; 549/337; 549/391
[58] Field of Search ................... 536/103; 514/58

[56] References Cited

U.S. PATENT DOCUMENTS 3,459,731  8/1969  Gramera et al. .............. 536/103

OTHER PUBLICATIONS

Chemical Abstracts 96:74507z (1982).
Chemical Abstracts 96:103983j (1982).
Chemical Abstracts 95:96336z (1981).

Primary Examiner—Ethel G. Love
Attorney, Agent, or Firm—Karl F. Ross; Herbert Dubno

[57] ABSTRACT

2,6-di-O-methyl-beta-cyclodextrin complexes of compounds of the formula (1a)

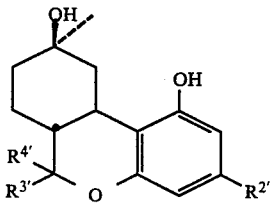

wherein $R^{2'}$ stands for $C_1$ to $C_{12}$ alkyl or a group of the formula

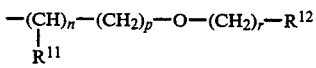

in which
$R^{11}$ is $C_1$ to $C_4$ alkyl;
$R^{12}$ is hydrogen or $C_1$ to $C_4$ alkyl;
n is 0 or 1;
p is 1 to 4;
r is 1 to 4; and
$R^{3'}$ and $R^{4'}$ are each $C_1$ to $C_4$ alkyl, or pharmaceutically salts thereof are disclosed, having analgesic activity.

8 Claims, No Drawings

DIBENZO[BD]PYRAN DERIVATIVES, PROCESS FOR THE PREPARATION THEREOF AND PHARMACEUTICAL COMPOSITIONS CONTAINING SAME

The present invention relates to partially new dibenzo[bd]pyran derivatives and salts thereof as well as new complexes of the compounds with 2,6-di-O-methyl-$\beta$--cyclodextrin.

The new compounds can be defined by the formula

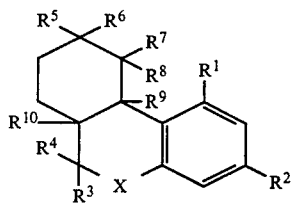

I wherein
$R^1$ stands for hydroxyl or $C_{1-4}$ acyloxy,
$R^2$ stands for $C_{1-12}$ alkyl, $C_{1-12}$ O-alkyl or O-aralkyl or a group of the formula

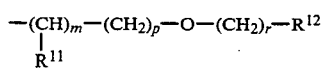

wherein
$R^{11}$ stands for $C_{1-4}$ alkyl,
$R^{12}$ represents hydrogen or $C_{1-4}$ O-alkyl
m stands for 0 to 1
p stands for 1 to 4
r stands for 1 to 4
$R^3$ represents hydrogen or $C_{1-4}$ alkyl,
$R^4$ represents hydrogen or $C_{1-4}$ alkyl or
$R^3$ and $R^4$ together form an oxo group,
X stands for oxygen or imino,
$R^5$ stands for hydroxyl and at the same time $R^6$, $R^7$, $R^8$, $R^9$ and $R^{10}$ stand for hydrogen or
$R^5$ represents $C_{1-4}$ alkyl and at the same time $R^8$, $R^9$ and $R^{10}$ stand for hydrogen and $R^6$ and $R^7$ together form a further chemical bond or
$R^5$ and $R^6$ together form an oxo group and at the same time
  (i) $R^7$, $R^8$, $R^9$ and $R^{10}$ represent hydrogen or
  (ii) $R^8$ and $R^{10}$ stand for hydrogen and $R^7$ and $R^9$ together form a further chemical bond or
  (iii) $R^7$ and $R^8$ stand for hydrogen and $R^9$ and $R^{10}$ together form a further chemical bond or
$R^5$ and $R^6$ together form a —O—(CH$_2$)$_2$—O— group and at the same time $R^7$ and $R^8$ stand for hydrogen and $R^9$ and $R^{10}$ together form a further chemical bond.

The complexes of the compounds of the formula I and of salts thereof with 2,6-di-O-methyl-$\beta$-cyclodextrin are new compounds. Compounds of the formula I are partially known and partially new.

Compounds of the formula I wherein
$R^1$ stands for hydroxyl
$R^2$ stands for a group of the general formula

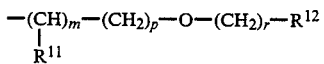

wherein $R^{11}$, $R^{12}$, m, p and r are as given above,
$R^3$ and $R^4$ stand for $C_{1-4}$ alkyl
X stands for oxygen and $R^5$ stands for hydroxyl and at the same time
$R^6$, $R^7$, $R^8$, $R^9$ and $R^{10}$ stand for hydrogen or
$R^5$ and $R^6$ together form an oxo group and at the same time
  (i) $R^7$, $R^8$, $R^9$ and $R^{10}$ stand for hydrogen or
  (ii) $R^8$ and $R^{10}$ stand for hydrogen and $R^7$ and $R^9$ together form a further chemical bond or
  (iii) $R^7$ and $R^8$ stand for hydrogen and $R^9$ and $R^{10}$ together form a chemical bond—are new.

Some representatives of the compounds of the formula I and salts thereof as well as complexes thereof with 2,6-di-O-methyl-$\beta$-cyclodextrin have analgesic and antemetic and narcosis potentiating activity and can be used as active ingredients of pharmaceutical compositions.

Compounds of the formulae

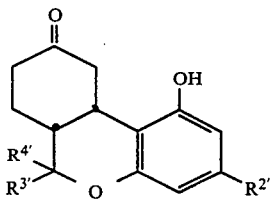

IB

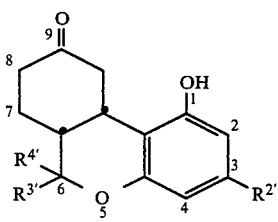

IC

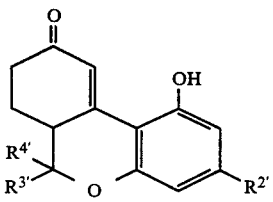

ID

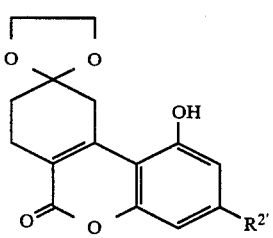

IE

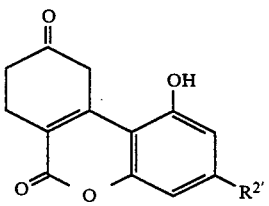

IF falling under the scope of the compounds of the formula I are starting materials or intermediate compounds of the preparation of other compounds of the formula

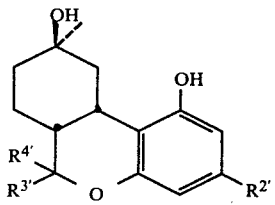

IA

Although many analgesics are available in therapy, none of them meets all the possible requirements.

Some analgesics, such as salicylic acid derivatives, show strong side effects and are not suitable for alleviating strong pain. Strong analgesics, such as d-propoxyphene, codeine and morphine have even greater side effects especially development of dependency.

It is obvious that highly effective analgetics which do not become habitual are needed.

Wilson et al. (J. Med. Chem., 19, 1165 1976) disclosed that the earlier disclosed conversion product of the mild analgesic $\Delta^9$ - tetra-hydrocannabinol [J. Med. Chem., 17, 475 (1974)] the 9-nor-9$\beta$-hydroxy-hexahydrocannabinol (1,9$\beta$-dihydroxy-3-n-pentyl-6a$\beta$,7,8,-9,10,10a$\alpha$-hexahydro-6,6-dimethyl-6H-dibenz/bd)pyrane is a strong analgesic, as strong as morphine. The $ED_{50}$ value determined by the "hot plate" test is 2.9 for the racemic compounds and 1.6 mg/kg for the levorotatory form (morphine. HCl 1.2 mg/kg). The $ED_{50}$ value determined by the "tail-flick" test is 1.71 mg/kg for the levorotatory form [B. R. Martin, W. L. Devey, M. D. Aceto, M. D. Adams, J. T. Earnhardt, J. M. Carney, Res. Commun. Chem. Pathol. and Pharmacol. 16, 187 (1977)].

$ED_{50}$ of ($\pm$)-1,9$\beta$-dihydroxy-6,6-dimethyl-3-(1,1-dimethyl-1-heptyl)-6a$\beta$,7,8,9,10,10a$\alpha$-hexahydro-6H-dibenzo(bd)-pyrane described in U.S. Pat. No. 3,507,885 and determined by the "tail-flick" test is p.o. 0.1-5 mg/kg and in the "mouse writhing" test p.o. 1.25 mg/kg.

No phenomena of addiction could be observed when the above compound or analogs thereof were used.

The synthesis of the racemic 9-nor-9$\beta$-hydroxy-hexahydro-cannabinol and other 3-alkyl substituted derivatives thereof as well as synthesis of their starting materials among others was disclosed in U.S. Pat. Nos. 3,507,885, 3,636,058, 4,054,581, 4,054,582 and 4,054,583.

In U.S. Pat. No. 3,649,650 such tetrahydro-6,6,9-trialkyl-6H-dibenzo[bd]pyrane derivatives are disclosed which contain $\omega$-dialkylamino-alkoxy in position 1 and which can be used as psychotherapeutics.

In DOS No. 2,415,697 the preparation of 1-hydroxy-6,6,9-trimethyl-hexahydro-dibenzo[bd]pyrane derivatives substituted in the 3-position by aralkyl, substituted aralkyl and pyridyl-alkyl and starting materials thereof, and their use as analgesics and as mild tranquilizers are disclosed.

Several patents relate to the preparation of 1-hydroxy-6,6,9-trimethyl-hexahydro[bd]pyranes substituted by a side-chain attached to the ring through an oxygen atom. U.S. Pat. Nos. 3,856,821, 3,864,492, 3,676,462, 3,547,952 and DOS No. 26,48,427 can be mentioned. The poor water solubility of the disclosed neutral and apolar compounds results in difficulties when applying said compounds. In animal tests ethanol and emulsifying agents were also added [J. C. Cradock, J. P. Davignon, C. L. Litterst, A. M. Guarine, J. Pharm. Pharmac., 25, 345 (1973)]. Several attempts have been made to solve this problem. Thus Thakkar et al. described the suspension in water of 1-hydroxy-3-alkyl-dibenzo[bd]pyranes by using polyvinyl-pyrrolidone [J. Pharm. Pharmacol., 29, 783 (1977)] and Cradock et al. [J. Pharm. Pharmacol, 25, 345 (1973)] suggested a mixture of ethanol-polyethoxylated vegetable oil for this purpose.

The subject of the AT-P No. 329 556 is the preparation of a biologically well utilizable polymorphic form of compounds of the same type.

The derivatives of tetracannabinol containing oxygen-containing side chain were earlier reported not to show any or a greatly reduced effect on the central nervous system when the oxygen is attached to the aromatic ring. [Bergel et. al. J. Chem. Soc. 1943, 286, Loev et. al. J. Med. Chem. 16, 1200 (1973)].

We have now found that compounds of the formula

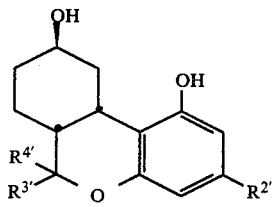

IA falling under the scope of the compounds of the formula I wherein $R^{2'}$ stands for $C_1$-$C_{12}$ alkyl or

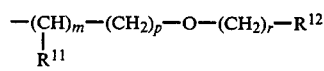

wherein $R^{11}$, $R^{12}$, m, p and r are as defined above and $R^{3'}$ and $R^{4'}$ stand for $C_{1-4}$ alkyl- i.e. 3-alkyl-1,9$\beta$-dihydroxy-6,6-dimethyl-6a,7,8,9,10,10a-hexahydro-6H-dibenzo-[bd]pyrane derivatives containing a side-chain comprising the oxygen atom in an ether bond formed with aliphatic carbons, are effective analgetics surpassing significantly the activity of morphine.

We have further found that the compounds of the formula I wherein $R^1$, $R^2$, $R^3$, $R^4$, $R^5$, $R^6$, $R^7$, $R^8$, $R^9$, $R^{10}$ and X as given above, can be included in cyclodextrin complexes increasing thereby the water solubility of the compounds and thus their biological activity. The inclusion complex formation with 2,6-di-0-methyl-$\beta$-cyclodextrin proved to be particularly advantageous. Not only can the active ingredient be administered in the form of aqueous solution but the analgesic activity is also unexpectedly increased.

In the hot-plate test using rats as test-animals suspended with 1% methyl cellulose ($\pm$)-1,9$\beta$-dihydroxy-6a$\beta$,7,8,9,10,10a$\alpha$-hexahydro-6,6-dimethyl-3-[(2RS)-5-methoxy-2-pentyl]-6H-dibenzo[bd]pyrane (CKN-30) and ($\pm$)-1,9$\beta$-dihydroxy-6a$\beta$,7,8,9,10,10a$\alpha$-hexahydro-6,6-dimethyl-3-[(2RS)-5-ethoxy-2-pentyl]-6H-dibenzo[bd]pyrane (CKN-49) show a moderate analgesic activity, the inclusion complexes thereof with 2,6-di-0-methyl-$\beta$-cyclodextrin show $ED_{50}$ values considerably surpassing that of morphine

| | $ED_{50}$ (mg/kg) | |
|---|---|---|
| | i.v. | s.c. |
| CKN-30 complex | 0.25 | 0.6 |
| CKN-49 complex | — | 0.074 |

| | ED$_{50}$ (mg/kg) | |
|---|---|---|
| | i.v. | s.c. |
| morphine | 3.6 | 4.6 |

The complexes according to the invention showed a significant narcosis potentiating activity too.

The narcosis time of 35 mg/kg of phenobarbital in rats is lengthened by ten times by using 0.1–0.25 mg/kg i.v. CKN-30 complex or 0.05 mg/kg of CKN-49 complex. In order to achieve similar activity more than 1 mg/kg of i.v. morphine was needed. For comparison it should be mentioned that in the "hot plate" test the ED$_{50}$ value of 9-nor-9$\beta$-hydroxy-hexahydro-cannabinol in the form of an aqueous suspension containing Emulphor emulsifying agent and ethanol is 2.9 mg/kg according to literature [R. S. Wilson, E. L. May, B. R. Martin, W. L. Dewey, J. Med. Chem., 19, 1165 (1976)], whereas ED$_{50}$ of the solution of the 2,6-di-0-methyl-$\beta$-cyclodextrin inclusion complex according to the invention in the same test was 0.6 (i.v.) and 0.9 (s.c.), thus the potentiating activity of the complex formation is obvious.

The present invention also provides a process for the preparation of the compounds of the formula I, salts and 2,6-di-0-methyl-cyclodextrin complexes thereof comprising (a) in order to prepare compounds of the formula IA falling within the scope of the formula I wherein $R^{2'}$ stands for $C_{1-12}$ alkyl or a group of the general formula

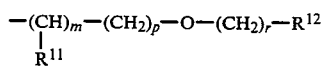

wherein $R^{11}$, $R^{12}$, m, p, and r are as defined above and $R^{3'}$ and $R^{4'}$ stand for $C_{1-4}$ alkyl- stereoselectively reducing a 6a,10a-trans-ketone of the formula

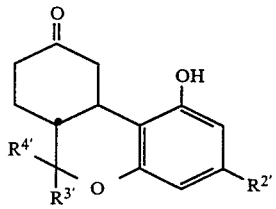

IB falling within the scope of the formula I—wherein $R^{2'}$ stands for $C_{1-12}$ alkyl or a group of the formula

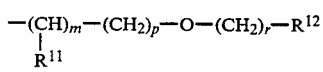

wherein $R^{11}$, $R^{12}$, m, p and r are as given above and $R^{3'}$ and $R^{4'}$ stand for $C_{1-14}$ alkyl or (b) in order to prepare 6a,10a-trans-ketones of the formula IB falling within the scope of the formula I—wherein $R^{2'}$, $R^{3'}$ and $R^{4'}$ are as defined above—isomerizing a 6a,10a-cis-ketone of the formula

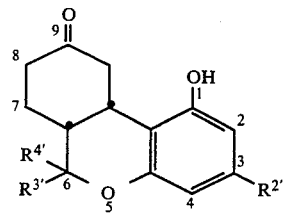

IC falling within the scope of the formula I—wherein $R^{2'}$, $R^{3'}$ and $R^{4'}$ are as defined above—with an electrophilic agent or (c) in order to prepare compounds of the formula IB, reducing a compound of the formula

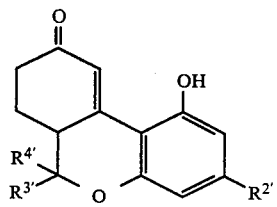

ID falling within the scope of the formula I—wherein $R^{2'}$, $R^{3'}$, $R^{4'}$ are as defined above—with alkali metals in liquid ammonia, or (d) in order to prepare compounds of the formula IC falling within the scope of the formula I—wherein $R^{2'}$, $R^{3'}$, $R^{4'}$ are as defined above—isomerising an oxocine derivative of the formula

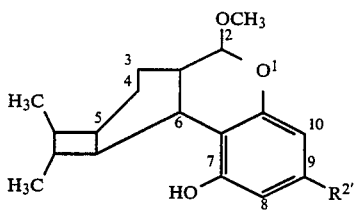

II wherein $R^{2'}$ is as defined above—with an electrophilic agent or (e) in order to obtain compounds of the formula IC, reacting a resorcine derivative of the formula

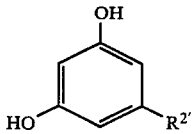

III wherein $R^{2'}$ is as defined above—with a cyclohexene derivative of the formula

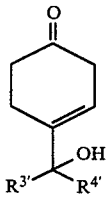

IV wherein $R^{3'}$ and $R^{4'}$ are as given above—in the presence of an electrophilic agent, or (f) in order to produce compounds of the formula ID—wherein the substituents are as defined above—reacting a compound of the formula

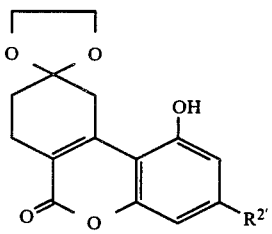
IE falling within the scope of the formula I—wherein $R^{2'}$ is as defined above—with alkyl magnesium bromide and hydrolyzing the formed intermediate product with an acid, or (g) in order to obtain compounds of the formula IE falling within the scope of the formula I—wherein $R^{2'}$ is as given above—reacting a compound of the formula

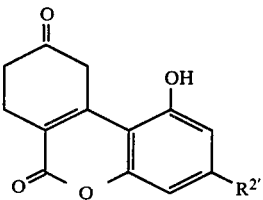
IF falling within the scope of the formula I—wherein $R^{2'}$ is as given above—with ethylene glycol or (h) in order to obtain compounds of the formula IF falling within the scope of the formula I—wherein $R^{2'}$ is as defined above—subjecting a compound of the formula

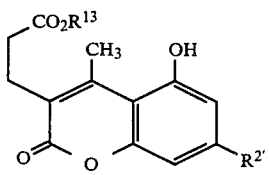
V wherein $R^{2'}$ is as defined above and $R^{13}$ stands for alkyl having 1 to 4 carbon atoms—to cyclization in the presence of a strong base, or (i) in order to obtain compounds of the formula IC—wherein the substituents are as defined above—reacting a compound of the formula III—wherein $R^{2'}$ is as defined above—with a compound of the formula

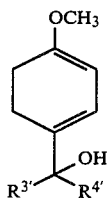
VI wherein $R^{3'}$ and $R^{4'}$ are as defined above—in the presence of an electrophilic agent and isomerizing the obtained compound of the formula II—wherein $R^{2'}$ is as defined above—as in variant d or (j) in order to obtain compounds of the formula IC—containing a group of the formula

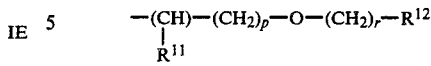

as $R^{2'}$, wherein $R^{11}$, $R^{12}$, p and r are as defined above and $R^{3'}$ and $R^{4'}$ are as given above—reacting a compound of the formula

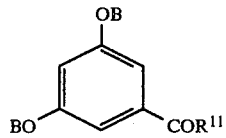
VII wherein $R^{11}$ is given above and B stands for protective group, preferably benzyl—with a Grignard reactant of the formula

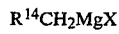
$R^{14}CH_2MgX$  VIII wherein $R^{14}$ stands for $-(CH_2)_{p-1}-O-(CH_2)_r-R^{12}$, wherein p, r and $R^{12}$ are defined above and X stands for halogen and subjecting the obtained compound of the formula

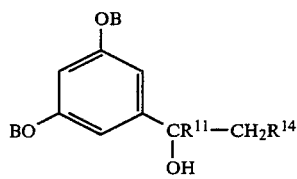
IX to dehydration—wherein $R^{11}$, $R^{14}$ and B are as defined above—and subjecting the obtained compound of the formula

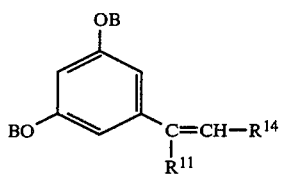
X wherein $R^{11}$, $R^{14}$ and B stand for the groups as above to hydrogenation and converting the obtained compound of the formula III containing as $R^{2'}$ a group of the formula

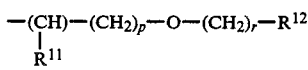

wherein $R^{11}$, $R^{12}$, p and r are as defined above and $R^{3'}$ and $R^{4'}$ as given above—to a compound of the formula IC by method given for process variants (e) or (i) or (k) in order to obtain a compound of the formula IC containing as $R^{2'}$ $-(CH_2)_3-O-(CH_2)_r-R^{12}$ —wherein $R^{12}$ and r are as defined above and $R^{3'}$ and $R^{4'}$ are given above—reacting a compound of the formula

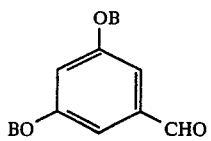

wherein B represents a protecting group, preferably a benzyl group,—with malonic acid, and reducing the obtained compound of the formula

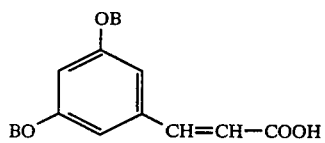

wherein B is as defined above—and mesylating the obtained compound of the formula

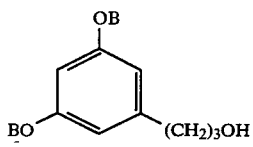

wherein B is as defined above—and reacting the obtained compound of the formula

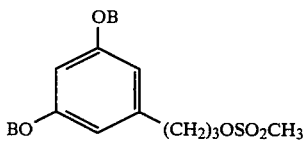

wherein B is as defined above with a compound of the formula $R^{12}$—$(CH_2)_r$—ONa    XV wherein $R^{12}$ and r are as defined above—removing the protecting groups and converting the compound of the formula III containing —$(CH_2)_3$—O—$(CH)_r$—$R^{12}$ as $R^{2'}$ $R^{12}$ and r are as defined abovce—wherein $R^{3'}$ and $R^{4'}$ are as given above to a compound of the formula IC by method given for process variants (e) or (i) or (1) in order to produce 2,6-di-O-methyl-β-cyclodextrin complexes of the compounds of the formula I, or salts thereof—wherein $R^1$, $R^2$, $R^3$, $R^4$, $R^5$, $R^6$, $R^7$, $R^8$, $R^9$, $R^{10}$ and X are as defined above—reacting a compound of the formula I or salt thereof—wherein the substituents are as defined above—with 2,6-di-O-methyl-β-cyclodextrin.

The alcohols of the formula IA can be prepared by stereoselective reduction of the ketones of the formula IB, preferably by using complex metal hydrides, such as sodium borohydride or lithium aluminum hydride at low temperature, preferably at −70° C. (process variant a).

6a,10a-trans-ketones of the formula IB are prepared by reacting 6a,10a-cis-ketones of the general formula IC with electrophilic agents preferably aluminum halides ($AlCl_3$, $AlBr_3$) (isomerization), (process variant b) or by reduction of the unsaturated ketones of the formula ID with alkali metals, preferably with lithium in liquid ammonia (process variant c).

Ketones of the formula IC can be prepared by isomerization of the oxocine derivatives of the formula II-—with electrophilic agents, preferably with tin (IV) chloride (process variant d), or by condensation of the resorcine derivatives of the formula III with cyclohexene derivatives of the formula IV, in the presence of electrophilic agents, preferably borontrifluoride-ethyletherate (process variant e).

Unsaturated ketones of the formula ID can be obtained by cyclization of the coumarine derivatives of the formula V in alkali medium, followed by the protection of the ketone group in the form of ethylene ketal, followed by reacting the obtained ketal with methyl magnesium bromide and hydrolyzing the product with acid (process variants (h)+(g)+(f)).

Oxocine derivatives of the formula II can be obtained from the resorcine derivatives of the formula III and cyclohexa-1,3-diene-derivatives of the formula VI by condensation in the presence of electrophilic agents, such as borotrifluoride-ethyletherate (process variant i).

Resorcine derivatives containing ether type oxygen in the sidechain of the formula III can be obtained by reacting acetophenone derivatives of the formula VII with Grignard reactants of the formula VIII, by dehydrating the obtained alcohol and by saturation the olephinic bond formed during the dehydration and by removing the protecting groups (process variant j) or by condensing aldehydes of the formula XI with malonic acid, followed by reduction with lithium aluminum hydride, mesylation of the obtained propanol derivative and reacting latter product with a sodium salt of alkoxy alcohol and finally removing the protecting groups (process variant k).

The 2,6-di-O-methyl-β-cyclodextrin inclusion complexes of the compounds of the formula I, can preferably be prepared by adding a compound of the formula I in ethanol under vigorous stirring to an aqueous solution of 2,6-di-O-methylβ-cyclodextrin, whereafter ethanol is removed in vacuo and if necessary a further ethanolic solution of the compound of the formula I is added to the obtained solution, and ethanol is removed again. The obtained solution of the inclusion complex is diluted with water. The molar ratio of the compound of the formula I and 2,6-di-O-methyl-β-cyclodextrin in the complexes according to the invention is preferably 2:1.

The further details of the invention can be found in the following Examples, which serve only for illustration and not for limitation.

EXAMPLE 1

(±)-1,9β-Dihydroxy-6aβ,7,8,9,10aα-hexahydro-6,6-dimethyl-3-[(2RS)-5-methoxy-2-pentyl]-6H-dibenzo[bd]pyrane A solution of 346 mg (1 mmole) of (±)-1-hydroxy-6,6aβ,7,8,9,10,10aα-hexahydro-6,6-dimethyl-3-[(2RS)-5-methoxy-2-pentyl]-9H-dibenzo[bd]pyrane-9-one in 4 ml. of ethanol is added to a solution of 150 mg. of sodium borohydride in 4 ml. of ethanol at −70° C. within 30 minutes. The mixture is warmed up to room temperature whereafter the excess of borohydride is decomposed with acetic acid, the solution is evaporated and the residue is extracted with chloroform after the addition of water and then dried and evaporated. The residue is crystallized from a mixture of ether and hexane. Colorless needles are obtained, (yield: 117 mg, 34%) double melting point: about 80° C. and 163° to 165° C.

¹H-NMR /100 MHz/: δ1.04 and 1.36 /s, 6H, C/CH₃/₂/, 1.15/d, J=6,8 Hz, 3H, CH-CH₃/, 0.9–2.4/m, aliphatic protons/, 3.32/s, 3H, OCH₃/, 3.8/m, 1H, 9-H$_a$/, 6.12 and 6.23/d, J=1.5 Hz, 1-1H, 2.6-H/, 6.9 /s, broad, 1H, OH/.

Similarly from (±)-1-hydroxy-6,6a62,7,8,10,10aα-hexahydro-3,6,6-trimethyl-9H-dibenzo[bd]pyran-9-one (±)-1,9β-dihydroxy-6aβ,7,8,9,10,10aβ-hexahydro-3,6,6-trimethyl-6H-dibenzo[bd]pyrane is prepared. M.p.: 233°–235° C.

¹H-NMR /200 MHz/: δ=0.9–1.6 /m, 6H, 6a,7,7,8,-10$_{aβ}$-H/, 1.03 és 1.35 [s, 6H, C/CH₃/₂], 1.43/s, 1H, 9-OH/, 1.89/m, J=12.5, 6.5 and 2.5 Hz, 1H, 8$_{eq}$-H/, 2.17 /d, J=0.74 Hz, 3H, 3-CH₃/, 2.49 /m, J=9.5, 2.5 és 0.6 Hz, 1H, 10a-H/, 3.43 /m, J=12.5, 4.0 and 2.5 Hz, 1H, 10$_{eq}$-H, 3.63 /m, sharpens upon D₂O, 1H, 9-H/, 4.67 /s, 1H, 1-OH/, 6.07 and 6.25 /q, J=0.74 Hz, 2H, 2.4-H/, from (±)-1-Hydroxy-6,6aβ,7,8,10,10aα-hexahydro-6,6-dimethyl-3-(3-methoxy-1-propyl)-9H-dibenzo[bd]-pyrane-9-one (±)-1,9β-dihydroxy-6aβ,7,8,9,10aα-hexahydro-6,6-dimethyl-3-(3-methoxy-1-propyl)-6-dibenzo[bd]pyrane is obtained; m.p.: 175°–176° C., ¹H-NMR/CDCl₃/: δ=1.04 and 1.37 /s, 6H, 6.6-CH₃/, 1.1–1.7/m, 7H,7,8,10-CH₂, 6aH/, 1.93 /mc, 2H, 2'-CH₂/, 2.15/mc, 1H, 10aH/, 2.50/mc, 2H, 1'-CH₂/, 3.33 /s, 3H, OCH₃/, 3.42 /t, J=6.5 Hz, 2H, 3'-CH₂/, 3.87/mc, 1H, 9-H/, 6.11/s, 1H, 1-OH/, 6.11 /d, J=2 Hz, Ar-H/, 6.25/d, J=2 Hz, 1H, Ar-H/, from (±)-1-Hydroxy-6,6aβ,7,8,10,10aα-hexahydro-6,6-dimethyl-3-[(2RS)-5-ethoxy-2-pentyl]-9H-dibenzo[bd]pyran-9-one (±)-1,9β-dihydroxy-6aβ,7,8,9,10,-10aα-hexahydro-6,6-dimethyl-3-[(2RS)-5-ethoxy-2-pentyl]-6H-dibenzo-[bd]pyrane is obtained, m.p.: 114°–118° C., ¹H-NMR /100 MHz, CDCl₃/: δ=1.04 and 1.35 [s, 6H, C/CH₃/₂], 1.1–1.25/m, 6H, 1'-CH₃, OCH₂CH₂/, 1.50/mc, 4H, 3',4'-CH₂/, 1.4–2.7/m, 9H, 2',6a,10a-H,7,8,10-CH₂/, 3.37/t, J=5.5 Hz, 2H, 5'-OCH₂/, 3.45 /q, J=7 Hz, 2H, OCH₂CH₃/, 3.83 /mc, 1H, 9-H/, 5.73 /s, 1H, OH/, and from (±)-1-Hydroxy-6,6aβ,7,8,10,10aα-hexahydro-6,6-dimethyl-3-[(2RS)-5-(2-methoxy-ethoxy)-2-pentyl]-9H-dibenzo[bd]pyran-9-one (±)-1,9β-dihydroxy-6aβ,7,8,9,10,10aα-hexahydro-6,6-dimethyl-3-[(2RS)-5-(2-methoxy-ethoxy)-2-pentyl]-9H-dibenzo[bd]pyrane is obtained, m.p.: 130°–132° C.

¹H-NMR /CDCl₃, 100 MHz/: δ=1.05 /s, 3H/ and 1.37 /s, 3H, 6.6-CH₃/, 1.16 /d, J=7 Hz, 1'-CH₃/, 1.54 /mc, 4H, 3',4'-CH₂/, 1.6–2.65 /m, 6H, 7,8,10-CH₂/, 3.37/s, 6H, OCH₂/, 3.52 /s, 3H, OMe/, 3.4–3.6/m, 1H/. 3.84/m, 9-H/, 5.85 /s, broad, 1-OH/, 6.10 /d, J=2 Hz, 1H, 4.6-H/.

EXAMPLE 2

(±)-1-Hydroxy-6,6aβ,7,8,10,10aα-hexahydro-6,6-dimethyl-3-[(2RS)-5-methoxy-2-pentyl]-9H-dibenzo[bd]-pyrane-9-one 0.35 g (±)-1-Hydroxy-6,6aβ,7,8,10,10aβ-hexahydro-6,6-dimethyl-3-[(2RS)-5-methoxy-2-pentyl]-9H-dibenzo[bd]pyrane-9-one are dissolved in 77.0 ml. of methylenechloride. To the solution 0.35 g. of aluminum chloride and 0.35 g of aluminium bromide are added. After stirring the solution for 5 hours at room temperature the solution is shaken with 5 ml of 1 N hydrochloric acid, the organic layer is separated, dried and the obtained isomer mixture is chromatographed on 20 g. of silicagel. (benzene-ethyl acetate=4:1). 100 mg. of pure product are obtained, which after recrystallization from hexane melts at 119°–121° C.

¹H-NMR /100 MHz/:δ=1.10 and 1.44 [s, 3-3H, /CH₃/₂C], 1.17/d, J=7 Hz, 3H, CH-CH₃/, 1.50 /pseudotriplett, 4H, 2',3'-CH₂/, 1.8–2.5/m, 9H/, 3.28 /s, 3H, OCH₃, 3.3 /t, 2H, 4'-CH₂, 4.06 /mc, ²J=15 Hz, ³J=3.5 Hz, ⁴J=1.5 Hz, 1H, 10-H$_{eq}$/, 6.13 /dd, J=2 Hz, 2H, 2.4-H/.

Similarly is prepared: from (±)-1-Hydroxy-6,6aβ-7,8,10,10aβ-hexahydro-6.6-dimethyl-3-(3-methoxy-1-propyl)-9H-dibenzo[bd]pyran-9-one (±)-1-Hydroxy-6,6aβ,7,8,10,10aα-hexahydro-6,6-dimethyl-3-(3-methoxy-1-propyl)-9H-dibenzo[bd]pyran-9-one, m.p.: 133°–134° C., ¹H-NMR /CDCl₃, 100 MHz/: δ=1.12 and 1.47 /s, 6H, 6.6-CH₃/, 1.4–2.0 /m, 3H, 6a-H, 7-CH₂/, 1.88 /mc, 2H, 2'-CH₂/, 2.10/mc, 1H, 10α-H/, 2.52 /t, J=8 Hz, 2H, 1-CH₂/, 2.5 /mc, 2H, 8-CH₂/, 2.90 /mc, 1H, 10a-H/, 3.33/s, 3H, OCH₃/, 3.41 /t, J=7 Hz, 2H, 3'-CH₂/, 4.04 /mc, ²J=15 Hz, ³J=4 Hz, ⁴J=1.5 Hz, 10β-H/, 6.23/dd, J=2 Hz, 2H, ArH/, 6.78 /s, 1H, OH/, from (±)-1-Hydroxy-6,6aβ,7,8,10,10aβ-hexahydro-6,6-dimethyl-3-[(2RS)-5-ethoxy-2-pentyl]-9H-dibenzo[bd]pyran-9-one (±)-1-Hydroxy-6,6aβ,7,8,10,10aα-hexahydro-6,6-dimethyl-3-[(2RS)-5-ethoxy-2-pentyl]-9H-dibenzo[bd]pyran-9-one, m.p.: 125°–133° C., ¹H-NMR /CDCl₃, 100 MHz/: δ=1.08 and 1.43 [s, 6H, C/CH₃/₂], 1.14 /t, J=7 Hz, CH₂CH₃/, 1.16 /d, J=7 Hz, 3H, 1'-CH₃/, 1.50 /mc, 4H, 3',4'-CH₂/, 3.38 /t, J=5.5 Hz, 2H, 5'-OCH₂/, 3.43 /q, J=7 Hz, 2H, OCH₂CH₃/, 4.08/dq, ²J=15, ³J=4, ⁴J=2 Hz, 1H, 10$_{eq}$-H/, 1.8–2.3 /m, 3H, 7-CH₂, 10$_{ax}$-H/, 2.4–2.6 /m, 3H, 2'-H, 8-CH₂/, 2.88/mc, ³J$_{10eq}$=4, ³J$_{6a}$=10.5, ³J$_{10ax}$=12.5 Hz, 1H, 10a-H/, 6.21 and 6.23/dd, J=2 Hz, 2H, 2,4-H/, 7.10/s, 1H, OH/, and from (±)-1-Hydroxy-6,6aβ,7,8,10,10aβ-hexahydro-6,6-dimethyl-3-[(2RS)-5-(2-methoxy-ethoxy)-2-pentyl]-9H-dibenzo[bd]pyran-9-one (±)-1-Hydroxy-6,6aβ,7,8,10,10aβ-hexahydro-6,6-dimethyl-3-[(2RS)-5-(2-methoxy-ethoxy)-2-pentyl]-9H-dibenzo[bd]-pyran-9-one, m.p.: 85°–92° C., ¹H-NMR /CDCl₃, 100 MHz/: δ=1.10 and 1.35 /s, 3-3H, 6,6-CH₃/, 1.25/d, J=7.2 Hz, 3H, 1'-CH₃/, 1.50/m, 4H, 3',4'-CH₂/, 1.9–2.6 /m, 6H/, 3.37/s, 6H, OCH₂/, 3.61 /s, 6H, OCH₃/, 4.07/d, J=15 Hz, 10aH/, 6.21/s, 2H, 4.6-H/, 7.33/s, broad, 1H, OH/.

EXAMPLE 3

(±)-1-Hydroxy-6,6aβ,7,8,10,10aα-hexahydro-3,6,6-trimethyl- 9H-dibenzo[bd]pyran-9-one 0.26 g. of metal lithium is dissolved in 250 ml. of dry liquid ammonia. To this solution 5.16 g. of 1--Hydroxy-6,6a,7,8-tetrahydro-3,6,6-trimethyl-9H-dibenzo- [bd]pyran-9-one are added. Ammonia is allowed to evaporate, to the residue water is added and the product is filtered off and recrystallized from ethanol. Yield: 2.0 g., m.p.: 214°–217° C., ¹H-NMR /CDCl₃, 100 MHz/:δ=1.11 és 1.47/s, 6H, 6,6-CH₃/, 1.2–1.8/m, 1H, 6a-H/,1.9–2.5/m, 3H, 7-CH₂, 10α-H/, 2.18/s, 1H, Ar-CH₃/, 2.7/mc, 2H, 8-CH₂/, 2.95/mc, 1H, 10a-H/, 4.12/d, ²J=15 Hz, 1H, 10β-H/, 6.28 s, 2H, 2,4-H/, 7.88/broad s, 1H, OH/.

EXAMPLE 4

(±)-1-Hydroxy-6,6aβ,7,8,10,10aβ-hexahydro-6,6-dimethyl-3-[(2RS)-5-methoxy-2-pentyl]-9H-dibenzo[bd]pyran-9-one 0.44g. of /±/-2-methoxy-9-//2RS/-5-methoxy-2-pentyl/- -3,4,5,6-tetrahydro-5-isopropylidene-2,6-methano-2H-1-benzooxocin-7olis dissolved in 8.8 ml. abs. dichloro-methane. To the solution 0.022 ml. (1.22 mmole) of water and 0.59 g. (0.264 ml., 2.26 mmole) of tin tetrachloride are added. After 2 hours stirring the mixture is shaken with 4 ml. of 1 N hydrochloric acid, the organic layer is separated and dried above magnesium sulphate and evaporated. The residue is triturated with n-hexane, whereupon the product crystallizes. The crystals are filtered by suction and washed with some ether-hexane mixture /1:4/. 0.25 g. /56%/ of a product is obtained, m.p.: 129°–131° C.

$^1$H-NMR /100 MHz/:δ = 1.16 /d, J=7Hz, 3H, CH-CH$_3$/, 1.32 and 1.38 [s, 3-Lb 3H, /CH$_3$/$_2$C]7, 1.54 /preseudotriplett, 4H, 2',3-CH$_2$/, 2.0-2.6/m/, 3.00/q, J$_1$=6Hz, J$_2$=16 Hz, 1H/, 3.14/d, or one half of q, J=7Hz, 1H/, 3.18/s, 3H, OMe/, 3.35 /t, J=7Hz, 2H, 4'-CH$_2$/, 3.53/t, J=7Hz, 1H/,6.17 and 6.24/d, J=2Hz, 1-1H, 2,4-H/, 6.45/s, /broad/, 1H, OH/.

Similarly is prepared: from (±) -2-Methoxy-9-[(2RS)-5-ethoxy-2-pentyl]-3,4,5,6-tetrahydro- 5-isopropylidene-2,6-methano-2H-1-benzoxocin-7-ol (±) -1Hydroxy-6,6aβ,7,8,10,10aβ-hexahydro-6,6-dimethyl-3-[(2RS) -5-ethoxy-2-pentyl]-9H-dibenzo[bd]pyran-9-one, m.p.: 123°–124° C., $^1$H-NMR/CDCl$_3$, 100 MHz/, δ=1.16/t, J=7Hz, 3H, CH$_2$CH$_3$/, 1.15/d, J=7Hz, 3H, 1'-CH$_3$/, 1.32 and 1.48 [s, 6H, C/CH$_3$/$_2$], 1.52/mc, 4H, 3',4'-CH$_2$/, 2.10/mc, 2H, CH$_2$/, 2.35-2.55/m, 3H, 2'-H, CH$_2$/, 3.10/mc, 2H, CH$_2$/, 3.37/t, J=5.5 Hz, 2H, 5'-OCH$_2$/, 3.44/q, J=7Hz, 2H, OCH$_2$CH$_3$/, 6.17 and 6.24/2xd, J=2Hz, 2,4-H/, 6.50/s, 1H, OH/, from (±) -2-methoxy-9-[(2RS)-5-(2-methoxy-ethoxy)-2-pentyl]-3,4,5,6-tetrahydro-5-isopropylidene-2,6-methano-2H-1-benzoxocin -7-ol(±) -1-Hydroxy-6,6aβ7,8.10,10aβ-hexahydro- -6,6-dimethyl-3-[(2RS) -5-(2-methoxy-ethoxy) -2-pentyl]-9H- dibenzo[bd]pyran-Z9-one, m.p.: 52°–57° C.

$^1$H-NMR[CDC]$_3$, 100 MHz/:δ=1.13 /d, J=7.2 Hz, 3H, 1'-CH$_3$/, 1.32 and 1.38/s, 6H, 6,6-CH$_3$/, 1.50/mc, 4H, 3',4'-CH$_2$/, 2.1/mc, 2H, 7-CH$_2$/, 2.35/mc, 4H, 8,10-CH$_2$/, 3.0-3.2/m, 2H/, 3.47/s, 6H, OCH$_2$/, 3.61/s, 6H, OMe/, 6.18/s, 2H, 2,4-H/, 7.12/s, 1H, OH/.

EXAMPLE 5

(±)-1-Hydroxy-6,6aβ,7,8,10,10aβ-hexahydro-6,6-dimethyl--3-(3-methoxy-1-propyl)-9H-dibenzo[bd]pyran-9-one 1.82 g. of 1,3-Dihydroxy-5-(3-methoxy-1-propyl)--benzene and 2.52 g. of freshly prepared 4-(2-hydroxy-2-propyl) -3-cyclchexene-1-one are dissolved in 200 ml. of absolute benzene. Within 30 minutes a solution of 2.5 ml of borontrifluoride etherate in 50 ml. of benzene is added. After 24 hours the solution is shaken out with a 10% aqueous hydrochloric acid solution, with 3 ×10 ml. 1N sodium hydroxide solution, then evaporated and the residue is purified by column chromatography/-silicagel, chloro-form-acetone 9:1/. Yield: 1.41 g., m.p. : 124°-144° C., $^1$H-NMR/CDCl$_3$, 100 MHz/:δ=1.41 and 1.47/s, 6H, 6,6-CH$_3$/, 1.85mc, 2H, 2'-CH$_2$/, 2.43/mc, 2H, 1'-CH$_2$/, 1.7-2.6/m, 6H/, 3.0-3.7/m, 2H/, 3.33/s, 3H, OCH$_3$/, 3.42/t, J=7 Hz, 3'-CH$_2$/, 6.22/dd, 2H, Ar-H/,6.2/covered s, 1H, OH/.

EXAMPLE 6

1-Hydroxy-6,6a,7,8-tetrahydro-3,6,6-trimethyl-9H--dibenzo[bd]pyran-9-one

Grignard reactant is prepared from 31.5 ml. of methyl iodide and 12.7 g. of magnesium in 250 ml. of abs. ether. To this reactant 300 ml. abs. benzene and 14.4 g of 1-hydroxy-3-methyl-7,8,9,10-tetrahydro-spiro (6H-dibenzo- [bd]pyran-9,2'-) 1',3'(-dioxolan)-6-one are added and the mixture is boiled for 44 hours under cooling with standing water. The inner temperature rise slowly to 75° C. The mixture is decomposed with 57.5 ml. of 1N hydrochloric acid and then with 210 ml. of hydrochloric acid of 1:1 dilution, the product is then filtered by suction and recrystallized from dimethylformamide. Yield: 5.4 g. m.p.: 265°–269° C., $^1$H-NMR/DMSO, 60 MHz/:δ=0.84 and 1.22 /s, 6H, 6,6-CH$_3$/, 2.93/s, 3H, 3-CH$_3$/, 2.1-2.8 /m, 5H, 6a-H, 7,8-CH$_2$/, 5.9 and 6.06/broads, 2H, 2,4-H/, 7.05/d, J=2.5Hz, 6a-H/, 10.32/s, 1H, Oh/.

EXAMPLE 7

1-Hydroxy-3-methyl-7,8,9,10-tetrahydro-spiro[H-dibenzo[bd]pyran-9,2'-[1',3']-dioxolan]-6-one 24.4 g. 1-Hydroxy-3-methyl-6,6a,7,8,-tetrahydro-9H--dibenzo [bd]pyran-6,9-dione, 410 ml. of xylene, 33 ml. of ethylene glycol and 0.33 g. of p-toluene sulfonic acid are heated for 6 hours under a water condensing trap. The product precipitated upon cooling. The product is filtered by suction. Yield: 26 g., m.p.: 246°-248° C. and 259°-260° C., $^1$H-NMR /CDCl$_3$, 60 MHz/:δ=1.71/t, J=6Hz, 2H, 7-CH$_2$/, 3.18/s, 3H, CH$_3$/, 3.1-3.5m, 2H, 8-CH$_2$/, 3.19/s, 2H, 10-CH$_2$/, 3.88/s, 4H, OCH$_2$C-H$_2$O/, 6.51/s, 2H, 2,4-H/.

EXAMPLE 8

1-Hydroxy-3-methyl-6,6a,7,8-tetrahydro-9H-dibenzo[bd]pyran-6.9-dione 91.6 g. of 3-(4,7-dimethyl-5-hydroxy-2H-1-benzopyran-2-on-3-yl) propionic acid ethyl ester [N.M. Shah, R. C. Shah, Ber/ dtsch. chem. Ges. 71, 2075 (1938)]are admixed with 72 g. of a 50 % oily suspension of sodium hydride. To this mixture 750 ml. of abs. dimethylsulfoxide are added dropwise at room temperature. Next day the mixture is poured to a mixture of 4 1 icy water and 250 ml. of concentrated hydrochloric acid. The product is filtered off and stirred with 1 1 saturated sodium hydrogen carbonate solution, filtered by suction and recrystallized from dimethylformamide. Yield: 52 ;l g., m.p.: 286°–188° C., $^1$H-NMR/DCDl$_3$, 60 MHz/:δ=2.36/s, 3H, 3-CH$_3$/, 2.6-2.9/m, 6H, 7,8,10-CH$_2$/, 6.65 and 6.78 /d, J.=2Hz, 2H, 2,4- H/.

EXAMPLE 9

(±)-2-Methoxy-9-[(2RS)-5-methoxy-2-pentyl]-3,4,5,6-tetrahydro -5-isopropylidene-2,6-methano-2H-1-benzoxocin-7-ol 1.05 g. of 1,3-dihydroxy-5-(5-methoxy-2-pentyl)- benzene and 1.06 g. (6 mmoles) of 1-(2-hydroxy-2-propyl)-4methoxy-1,4-cyclohexadiene [R.A. Archer et. al. J.

Org. Chem., 42, 2277 (1977)]are dissolved in 25 ml. of abs. benzene. 0.5 ml. (3.4 mmoles) of borontrifluoride etherate are added and the mixture is stirred at room temperature for 5 hours. Further 0.40 g. (2.4 mmoles) diene are added and the mixture is stirred overnight. The solution is poured off from the precipitated gum and extracted with 3 × 10 ml. of 1 N sodium hydroxide. The benzene solution is dried, evaporated and the residue is chromatographed on a column with a 8.1 mixture of benzene: ethyl acetate. The product is a colorless resin.

$^1$H-NMR/CDCl$_3$, 100 MHz/:δ=1.19/d, J=6.5 Hz, 3H, C$^1$H-CH$_3$/, 1.54 /mc, 4H, 2'3'-CH$_2$/, 1.67 and 1.93 [s, 3-3H, /CH$_3$/$_2$C=],
1.7–2.7 /m, 6H, 3,4,11-CH$_2$/, 3.28/s, 3H, 2-OMe/, 3.41/s, 3H, 4'-OMe/, 3.35/t, J=7Hz, 2H, 4'-CH$_2$/, 4.32/s, broad/, 1H, 6-H/,4.78/s, 1H, exchanged with D$_2$O, OH/, 6.16 and 6.37 /d, J=2 Hz, 1-1H, 8,10-H/.

Similarly from 1,3-dihydroxy-5-(5-ethoxy-2-pentyl)-benzene (±)-2-methoxy-9- [(2RS)-5-ethoxy-2-pentyl]-3,4,5,6-tetrahydro-5-isopropylidene-2,6-methano-2H-1-benzoxocin-7-ol, colorless resin, as prepared:

$^1$H-NMR /CDCl$^3$, 100 MHz/:δ=1.17/t, J=7Hz, 3H, CH$_2$CH$_3$/, 1.19/d, J=7 Hz, 3H, 1'-CH$_3$/, 1.4–2.0/m, 6H,2',3'-CH$_2$, CH$_2$/, 1.46 and 1.93 [s, 6H, C/CH$_3$/$_2$], 2.15mc, 2H, CH$_2$/, 2.4–2.6/m, 3H, 2'-H, CH$_2$/, 3.3–3.6 /m, 4H, OCH$_2$/, 4.42/s, 3H, OCH$_3$/, 4.12/mc, 1H, 6-H/, 4.92/s, 1H, OH/, 6.16 and 6.35/2×d, J=2Hz, 8,10-H/, and from 1,3-dihydroxy-5-5-(2-methoxy-ethoxy)-2-pentyl]benzene (±)-2-methoxy -9-[(2RS)-5-(2-methoxy-ethoxy)-2- -pentyl]-3,4,5,6-tetrahydro-5-isopropylidene-2,6-methano- -2H-1-benzoxocin-7-ol, colorless resin is prepared:

$^1$H-NMR/CDCl$_3$, 100 MHz/:δ=1.05/d, J=7.2Hz, 3H, 1'-CH$_3$/, 1.50/mc, 3',4'CH$_2$/, 1.66 and 1.92/s, 2×3H, [=C/CH$_3$/$_2$],
3.35/s, 6H, OCH$_2$/, 3.40 and 3.52/s, 6H, OMe/, 4.3/s broad, 1H, 6-H/, 5.8/s, broad, 1H, OH/, 6.10 and 6.28/s, 2H, 8,10-H/.

EXAMPLE 10

1,3-Dihydroxy-5-(5-methoxy-2-pentyl)-benzene 1.83 g. magnesium is activated with some iodine and 85 ml. of abs. ether are added. Under vigorous stirring 8.3 g. of 1-chloro-3-methoxy-propane are added dropwise within 2 hours. The mixture is stirred for another 30 minutes whereafter 16.7 g. of 3,5-dibenzyloxy-acetophenone dissolved in 65 ml. abs. ether are added dropwise to the reactant. The mixture is stirred for 30 minutes and the mixture is decomposed with 10% sulphuric acid and the ethereal layer is separated, and shaken out with 20 ml. of saturated sodium carbonate solution and saturated salt solution and finally evaporated. The residue is heated under stirring in 120 ml. of benzene together with 1.0 g. of p-toluene-sulfonic acid for 1 hour. The mixture is shaken thoroughly with 1.0 g. of dried potassium carbonate, filtered and evaporated in vacuo. The residue is dissolved in 300 ml. of methanol and hydrogenated above 3 g. of prehydrated 10% palladium on charcoal catalyst at room temperature. The catalyst is removed by filtration and the solution is evaporated. The product is a gum. Yield: 9.5–10.0 g. boiling point: 180°–190° C. (at 20 Pa), $^1$H-NMR/CDCl$_3$, 60 MHz/:δ=1.18/d, J=7.5 Hz, 3H, 1-CH$_3$/, 2,50/mc, 4H, 3,4-CH$_2$/, 2.50/mc, 1H, 2-H/, 3.29/s, 3H, OCH$_3$/, 3.37/t, J=6 Hz, 2H, 5-CH$_2$, 6.20/mc, 3H, 2',4',6'-H/, 6.4/s /broad/, 2H, OH/.

Similarly is obtained from 3,5-dibenzyloxy-acetophenone and 3-ethoxy-1-chloro-propane the 1,3-dihydroxy-5-(5-ethoxy-2-pentyl)-benzene, colorless gum, $^1$H-NMR/CDCl$_3$, 60 MHz/:δ=1.18/d, J=7.5 Hz, 3H, 1-CH$_3$/, 1.18/t, J=7.5 Hz, 3H CH$_2$CH$_3$/, 1.40/m, 4H, 3,4-CH$_2$/, 2.5/m, 1H, 2-H/, 3.3–3.7/m, 4H, OCH$_2$/, 6.25/s, 3H, aromatic-H/, 6.9broad s, 2H, OH/, and from 3.5-dibenzyloxy-acetophenone and 3-(2-methoxy-ethoxy)-1-chloro-propane 1,3-dihydroxy-5-[5-(2-methoxy-ethoxy(-2-pentyl]-benzene, colorless gum, $^1$H-NMR/CDCl$_3$, 60 MHz/:δ=1.08/d, J=6.5 Hz, 1-CH$_3$/, 1.5mc, 3,4-CH$_2$/, 2.5/mc, 1H, 2-H/, 3.30/s, 4H, OCH$_2$/, 3.50/s, 5H, OCH$_3$, OCH$_2$/, 6.15/s 3H, 2',4',6'-H/, 6.35/s, broad s, 2H, OH/.

EXAMPLE 11

1,3-Dihydroxy-5-(3-methoxy-1-propyl)-benzene 3.18 g. of 3,5-dibenzyloxy-benzaldehyde [L.A. Svensson, Kem. Tidskr., 87, 289 (1975)] and 1.6 g. of malonic acid are stirred in a mixture of 8 ml. of pyridine and 0.1 ml. of piperidine for 3 hours at 100° C. 25 ml. of 15% hydrochloric acid are then added, whereafter the product is filtered by suction, washed with water and dried. The crude product is crystallized from 150 ml. of methanol and 3 g. of 3-(3,5-dibenzyloxy-phenyl)-propenoic acid melting at 154°–156° C. are obtained. The product is suspended in 250 ml. of abs. ether, 0.90 g. of lithium aluminum hydride is added and the mixture is heated under stirring for 5 hours. After cooling the excess hydride is decomposed by acetone and acidified with 100 ml. of 10% hydrochloric acid. The two layers are separated and the aqueous layer is shaken out with ether again, the combined organic layer is washed with water, dried on magnesium sulphate and evaporated. 2.88 g. of 3-(3,5-dibenzyloxy-phenyl)-1propanol are obtained, m.p.: after recrystallization from n-hexane: 48°–50° C. 5.47 g. of the above alcohol are dissolved in 30 ml. of abs. pyridine and 2.26 g. (1.5 ml., 0.020 mole) of methane sulfonic acid chloride are added and the mixture is poured after 30 minutes to a mixture of 300 g of ice and 75 ml. of cc. HCl. The product is extracted with 125 ml. of dichloromethane and the organic layer is washed with 2×20 ml. of saturated hydrochloric acid solution, dried above magnesium sulphate and evaporated. 6.2 g. of 3-(3,5-dibenzyloxy-phenyl)-1-methanesulfonyloxy-propane are obtained, from which 2.60 g. are heated for 15 minutes with 20 ml. of 1 N sodium methylate and the solution is poured to 220 ml. of 1% hydrochloric acid solution. The product is extracted with dichloromethane, the extract is dried and evaporated. The residue (1.9 g.) is subjected to column chromatography and as eluants benzene and methyl ethyl ketone solvents are used. 1.30 g. of 1-(3,5-dibenzyloxy-phenyl)-3-methoxy-propane are obtaned as colorless oil, $^1$H-NMR/CDCl$_3$, 60 MHz/:δ=1.9/mc, 2H, 2-CH$_2$/, 2.65/t, J=8.5 Hz, 2H, 3-CH$_2$/, 3.38/s, 3H, OMe/; 3.42/covered, 2H, 1-CH$_2$/, 3.50/s, 2H, CH$_2$O/, 4.93/s, 4H, OCH$_2$Ph/, 6.37/s, 3H, 2',4',6'-H/, 7.25/s, 10H, C$_6$H$_5$/.

1.30 g. of the above methoxy compound are debenzylated in 25 ml. methanol by catalytic hydrogenation in the presence of 0.7 g. 10% palladium on charcoal catalyst. After processing 10.63 g. of 1,3-dihydroxy-5-

(3-methoxy-1-propyl)-benzene are obtained as an oily product.

EXAMPLE 12

3.75 g. of 2,6-di-O-methyl-β-cyclodextrin are dissolved in 20 ml. of distilled water. A solution of 125 mg. (±)--1,9β-dihydroxy-6,6-dimethyl-3-pentyl-6aβ7,8,10,-10aα-hexahydro-6H-dibenzo[bd]pyrane in 5 ml. 96% ethanol is added to the solution at room temperature under vigorous stirring. The solution is evaporated in vacuo to a volume of 15 ml. and supplemented with distilled water to 20 ml. Another 125 mg. of active ingredient dissolved in 5 ml 96% ethanol is added and the solution is evaporated to 15 ml. The solution is filled up to a final volume of 25 ml. The active ingredient content is determined in 50% aqueous ethanol spectrophotometrically: 10.0 mg/ml. The inclusion complex formation is proved by the comparison of the $^{13}$C NMR spectra of the active ingredient and its complex. The chemical shifts of the following signals is significantly changed upon complex formation/the data in brackets are the data of the complex/:

δ=22.50 /22.26/, 27.93 /28.28/, 33.75 /33.95/, 35.55 /35.74/, 48.79 /49.60/, 76.56 /77.64/, 107.94 /108.41/, 108.78 /109.22/, 109.54 /110.83/, 154.88 /155.56/ p.p.m.

Similarly are prepared the aqueous solutions of the 2,6-di-O-methyl-β-cyclodextrin inclusion complexes of (±)--1,9β-dihydroxy-6,6-dimethyl-3-(5-methoxy-2-pentyl)-6aβ,7,8,9,10,10aα-hexahydro-6H-dibenzo[bd]pyrane, (±)-1.9β-dihydroxy-6,6-dimethyl-3-(5-ethoxy-2-pentyl)-6aβ,7,8,9,10,10aα-hexahydro-6H-dibenzo[bd]-pyrane, 1,9βdihydroxy-6,6-dimethyl-3- (2,2-dimethylheptyl)-6,6a,7,8,9,10,10a-hexahydro-9H-dibenzo[bd-]pyran,6,6,9-trimethyl-1-hydroxy-3-pentyl-6a,7,8,10a-tetrahydro-6H-dibenzo[bd]pyrane and 1-acetoxy-5,6,6aβ,7,8,9,10,10aα-octahydro-9β-hydroxy-6βmethyl-3-(5-phenyl-2-pentyloxy)-phenanthridine-hydrochloride.

We claim:

1. A 2,6-di-O-methyl-beta-cyclodextrin-complex of a compound of the Formula (Ia)

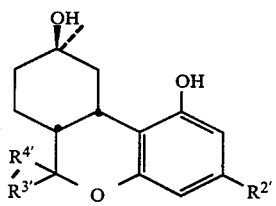

wherein R$^{2'}$stands for C$_1$-C$_{12}$ alkyl or a group of the Formula

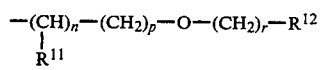

in which
R$^{11}$ is C$_1$-C$_4$ alkyl;
R$^{12}$ is hydrogen or C$_1$-C$_4$ alkyl;
n is 0 or 1;
p is 1 to 4;
r is 1 to 4; and
R$^{3'}$and R$^{4'}$are each C$_1$-C$_4$ alkyl, or a pharmaceutically acceptable salt thereof.

2. The 2,6-di-O-methyl-beta-cyclodextrix-complex of the compound of the Formula (I) as defined in claim 1 wherein the compound of the Formula (I) is:
1,9-beta-dihydroxy-6abeta,7,8,9,10,10aalpha-hexahydro-6,6-dimethyl-3-[(2RS)-5-methoxy-2-pentyl]-6H-dibenzo[bd]pyran;
1,9-beta-dihydroxy-6abeta-7,8,9,10,10aalpha-hexahydro-6,6-dimethyl-3[(2RS)-5-ethoxy-2-pentyl]-6H-dibenzo[bd]pyran; or
1,9-beta-dihydroxy-3-pentyl-6a,7,8,9,10,10a-hexahydro-6,6-dimethyl-6H-dibenzo[bd]pyran, or a pharmaceutically acceptable salt thereof.

3. The 2,6-di-O-methyl-beta-cyclodextrin complex of the compound of the Formula (I) as defined in claim 1 wherein R$^{2'}$is the group of the Formula

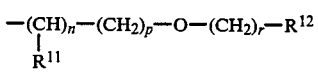

or a pharmaceutically acceptable salt thereof.

4. 2,6-di-O-methyl-beta-cyclodextrin complex of (±)-1,9β-dihydroxy-6aβ,7,8,9,10,10aα-hexahydro-6.6-dimethyl-3-((2RS)-5-methoxy-2-pentyl)-6H-dibenzo (bd) -pyrane and salts thereof as defined in claim 1.

5. Complex of 1,9β-Dihydroxy-6aβ,7,8,9,10,10aα-hexahydro-6,6-dimethyl-3-[(2RS)-5-methoxy-2pentyl]-6H-dibenzo[bd]pyrane with 2,6-di-O-methyl-62-cyclodextrin as defined in claim 1.

6. 2,6-di-O-methyl-62-cyclodextrin complex of 1,9β-dihydroxy-3-pentyl-6a,7,8,9,10,10a-hexahydro-6,6-dimethyl-6H-dibenzo[bd]pyrane as defined in claim 1.

7. An analgesic composition containing as active ingredient a therapeutically effective amount of the 2,6-di-O-methyl-62-cyclodextrin complex of compounds of the formula I or pharmaceutically acceptable salts thereof as defined in claim 1, along with a pharmaceutically acceptable inert carrier.

8. An analgesic method of treatment which comprises the step of administering to an animal subject in need of said treatment an analgesically effective amount of the 2,6-di-O-methyl-betl-cyclodextrin complex of the compound of the Formula (1a) as defined in claim 1, or a pharmaceutically acceptable salt thereof.

* * * * *